United States Patent [19]

Wallshein

[11] 4,054,997

[45] Oct. 25, 1977

[54] ORTHODONTIC ELASTIC APPLIANCE

[76] Inventor: Melvin Wallshein, 8645 Bay Parkway, Brooklyn, N.Y. 11214

[21] Appl. No.: 719,829

[22] Filed: Sept. 2, 1976

Related U.S. Application Data

[63] Continuation of Ser. No. 629,918, Nov. 7, 1975, abandoned, which is a continuation-in-part of Ser. No. 566,752, April 10, 1975, which is a continuation-in-part of Ser. No. 310,574, Nov. 29, 1974, Pat. No. 3,879,850.

[51] Int. Cl.$^2$ ............................................. A61C 7/00
[52] U.S. Cl. ................................................... 32/14 A
[58] Field of Search ................... 32/14 A, 14 B, 14 E

[56] References Cited

U.S. PATENT DOCUMENTS

| 3,530,583 | 9/1970 | Klein et al. | 32/14 A |
| 3,593,421 | 7/1971 | Brader | 32/14 A |

Primary Examiner—Robert Peshock
Attorney, Agent, or Firm—Flynn & Frishauf

[57] ABSTRACT

An orthodontic elastic appliance for use with an orthodontic bracket means which defines a channel, or for use directly on teeth, comprises a plurality of closed loops of elastic material interconnected by elastic connecting means coupled between adjacent closed loops. The closed loops are provided with engaging means on a surface thereof, the engaging means being dimensioned and shaped such that when a loop is stretched and is at least partially engaged with a bracket and/or a tooth, the engaging means abuttingly engages at least a portion of an engaging and retaining surface of a bracket, or at least a portion of the tooth, to substantially prevent the engaged elastic loop from shifting its position relative to the bracket means or tooth on which it is mounted.

92 Claims, 28 Drawing Figures

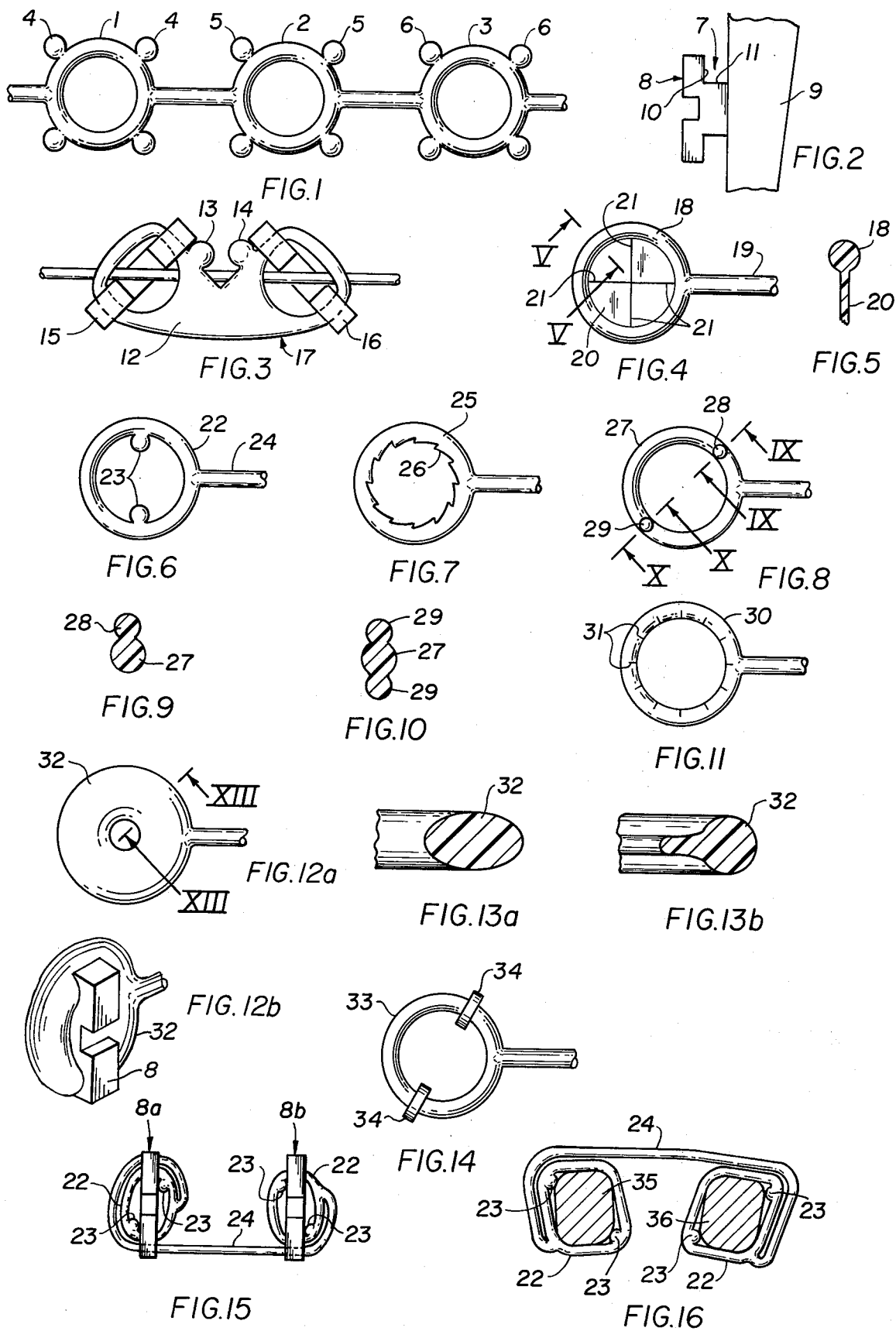

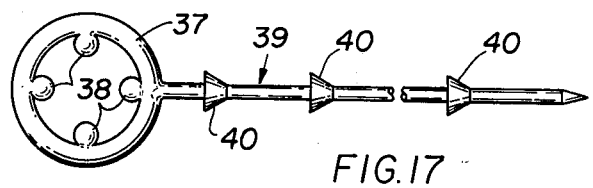
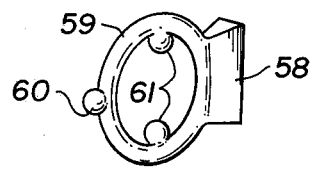
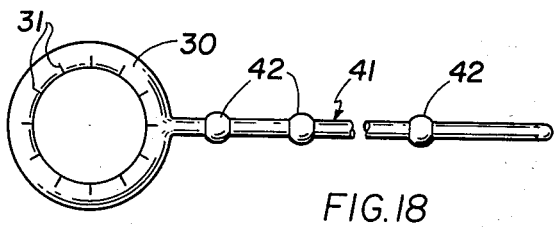
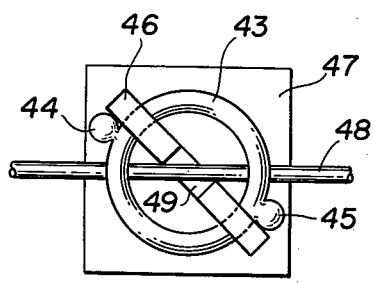
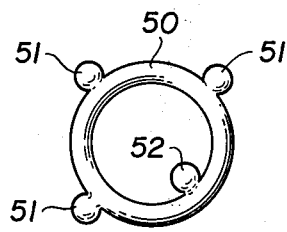
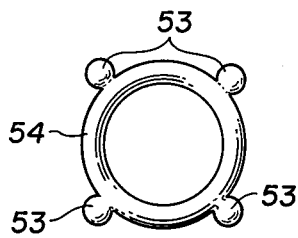
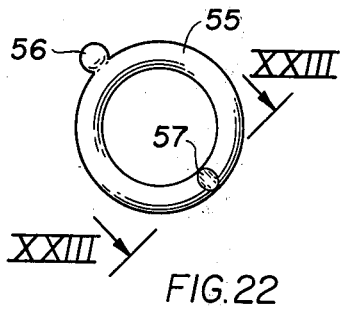
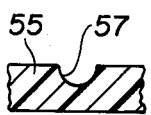
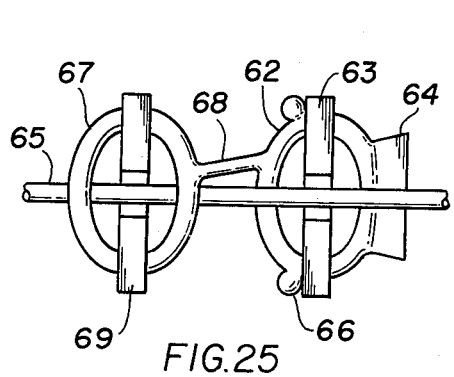
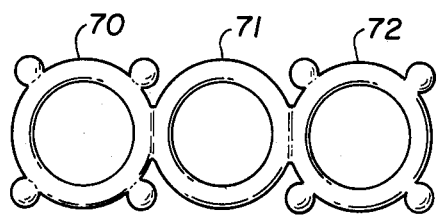

ORTHODONTIC ELASTIC APPLIANCE

CROSS-REFERENCE TO RELATED APPLICATION

This is a continuation of application Ser. No. 629,918, filed Nov. 7, 1975, and now abandoned, a continuation-in-part of U.S. application Ser. No. 566,752, filed Apr. 10, 1975, which in turn is a continuation-in-part of U.S. application Ser. No. 310,574, filed Nov. 29, 1974, now U.S. Pat. No. 3,879,850, issued Apr. 29, 1975 to Melvin Wallshein.

CROSS-REFERENCE TO RELATED PATENTS

U.S. Pat. No. 3,803,715, issued Apr. 16, 1974 to Melvin Wallshein; and

U.S. Pat. No. 3,896,549, issued July 29, 1975 to Melvin Wallshein.

The entire contents of U.S. Pat. Nos. 3,803,715 and 3,896,549 are incorporated herein by reference.

BACKGROUND OF THE INVENTION

The present invention generally relates to orthodontic elastic appliances, and particularly to an elastic appliance for cooperating with an orthodontic bracket means connected to at least one tooth, for transmitting generally rotational forces to the bracket means to cause corresponding movements of the teeth to which the bracket means are connected.

The object of the present invention is to provide an orthodontic elastic appliance which is relatively easy to use, which operates with substantially all types of brackets, is usable in a great variety of different situations and which is simple to manufacture.

SUMMARY OF THE INVENTION

In accordance with one aspect of the present invention, there is provided an orthodontic elastic appliance for use with orthodontic bracket means mountable on teeth, the bracket means defining an opening of predetermined crosssectional dimension adapted to receive at least a portion of the orthodontic elastic appliance therein, the bracket opening defined by at least one of said brackets having at least one engaging and retaining surface adjacent thereto. The elastic appliance comprises: a plurality of closed loops of elastic material, and elastic connecting means coupled between adjacent closed loops, each of the loops being adapted to pass through at least a portion of an opening of a bracket means so as to be mounted on the bracket means. Engaging means is provided on a surface of at least one of the elastic loops, the engaging means on the at least one elastic loop being dimensioned and shaped such that when the at least one elastic loop is stretched and is at least partially engaged in an opening defined by one of the bracket means, the engaging means of the at least one elastic loop abuttingly engages at least a portion of the at least one engaging and retaining surface of the bracket means to substantially prevent the engaged elastic loop from shifting its position relative to the bracket means on which it is mounted.

In accordance with a further feature of the present invention, an orthodontic elastic appliance mountable on teeth comprises a plurality of closed loops of elastic material having an inner periphery substantially smaller than the outer periphery of the tooth on which it is to be mounted, elastic connecting means coupled between adjacent closed loops, and engaging means on an inner surface of at least one of the elastic loops, the engaging means being dimensioned and shaped such that when said at least one elastic loop is stretched and is engaged around the outer periphery of a tooth the engaging means on the inner surface of the at least one elastic loop non-slidingly engages at least a portion of the outer periphery of the tooth to substantially prevent the stretched and engaged elastic loop from shifting its position relative to the tooth around which it is mounted.

The loops of the present invention may be provided in strip form with elastic connecting means between adjacent loops, and the strip may be cut to desired lengths by the user.

Preferably the elastic appliance is integrally molded from an elastic material.

BRIEF DESCRIPTION OF THE DRAWINGS

FIG. 1 illustrates an elastic band according to the present invention in strip form which may be cut to desired lengths by a user;

FIG. 2 illustrates a typical bracket attached to a tooth with which the present invention is useful;

FIG. 3 illustrates another embodiment of the invention mounted between two brackets respectively mounted on two teeth;

FIG. 4 illustrates a further example of an elastic band according to the present invention;

FIG. 5 is a partial cross-sectional view of the embodiment of FIG. 4;

FIG. 6 illustrates another embodiment of the invention;

FIG. 7 illustrates still another embodiment of the present invention;

FIG. 8 illustrates a still further embodiment of the present invention;

FIG. 9 is a cross-sectional view of the embodiment of FIG. 8 taken along the line IX—IX;

FIG. 10 is a cross-sectional view of the embodiment of FIG. 8 taken along the line X—X;

FIG. 11 illustrates an additional embodiment of the present invention;

FIGS. 12a and 12b illustrate a still further embodiment of the present invention;

FIG. 12b showing the device of FIG. 12a mounted on a bracket.

FIGS. 13a and 13b illustrate cross-sectional views of typical embodiments of FIG. 12 taken along the line XIII—XIII in FIG. 12;

FIG. 14 illustrates a still further embodiment of the present invention;

FIG. 15 illustrates the use of the embodiment of FIG. 6 between brackets to provide rotational forces to teeth;

FIG. 16 illustrates the embodiment of FIG. 6 as applied directly to teeth to provide rotational forces to teeth about their longitudinal axes;

FIG. 17 illustrates a further embodiment of the invention utilizing a single elastic loop in combination with an elongated elastic strand;

FIG. 18 illustrates a still further embodiment of the present invention along the lines of FIG. 17, but using a different type of elastic loop and elastic strand;

FIGS. 19-23 illustrate other related embodiments of the present invention, and

FIGS. 24-26 show still further modifications of the present invention.

DETAILED DESCRIPTION OF THE DRAWINGS

In my prior U.S. Pat. No. 3,879,850 orthodontic elastic appliances are disclosed in which protuberance means, such as nodules, are provided on the elastic appliance for cooperation with orthodontic brackets which define openings of predetermined cross-sectional dimension. In accordance with U.S. Pat. No. 3,879,850, the protuberance means are larger than the cross-sectional dimension of the opening or channel defined by the bracket so that the nodules or protuberance means cannot pass through the openings. The entire contents of U.S. Pat. No. 3,879, 850 is incorporated herein by references.

In my copending application Ser. No. 566,752, filed Apr. 10, 1975, which is a continuation-in-part of the application from which said U.S. Pat. No. 3,879,850 matured, there is disclosed elongated orthodontic elastic appliances with engaging means thereon which are adapted to engage an engaging and retaining surface of an opening or channel defined by a bracket. In accordance with said application Ser. No. 566,752, the engaging means, which may be nodules and/or protuberance means, need not be larger than the cross-sectional dimension of the opening or channel defined by the bracket. The entire contents of said U.S. application Ser. No. 566,752, filed Apr. 10, 1975, is incorporated herein by reference.

In accordance with the present invention, an orthodontic elastic appliance, having a plurality of closed loops of elastic material interconnected by an elastic connecting means is provided. At least one of the closed loops has engaging means on at least one surface thereof for engaging a bracket or a tooth directly in a substantially non-rotational manner. By non-rotationally applying the closed loops to the brackets and/or directly to the teeth, urging forces are generated in order to torque, rotate or otherwise move one or more teeth from misaligned positions to desired positions under the influence of the stressed or stretched elastic band.

Referring to FIG. 1, an elastic appliance of the present invention comprises, for example, a plurality of elastic loops 1, 2, 3, each of which has respective nodules or protuberances 4, 5, 6 on a surface thereof. The nodules or protuberances need not have a larger cross-sectional or lateral dimension larger than the cross-sectional dimension of the opening 7 of a bracket 8 mounted on a tooth 9 as shown in FIG. 2. The opening 7 has, for example, engaging and retaining surfaces 10, 11 against which the nodules or protuberances 4, 5, 6 are adapted to abuttingly engage when the loops 1, 2, 3 are stretched to engage the opening 7 of the bracket 8. Non-rotational engagement with the bracket is achieved by virtue of the fact that when the loop 1, 2, 3 is stretched over the bracket 8 to engage the opening 7 thereof, the engagement is tight such that the loop leaves the bracket at an angle, tending to press the protuberance or nodules 4, 5, 6, whichever is applicable, against an engaging and retaining surface 10, 11. There is no need for the nodules to be of larger dimension than the openings of the channels, as required by my prior U.S. Pat. No. 3,879,850. While FIG. 2 illustrates one type of bracket 8, it should be clear that the present invention is useful with any type of bracket which defines an opening 7 by itself or in cooperation with a portion of a tooth, such as tooth 9 of FIG. 2, and wherein the loop is adapted to engage an opening defined by the bracket.

FIG. 3 illustrates another example of the present invention wherein an elastic member 12 defines loops at opposite ends thereof, and has protuberances or nodules 13, 14 extending therefrom for non-rotationally engaging the brackets 15, 16, respectively. The brackets 15, 16 are angularly oriented on a surface of a tooth and are fixedly secured to the tooth so as to apply the proper rotational forces to the tooth which result from the stretching of the member 12 when applying the member 12 to the brackets. The most stressed portion of member 12 is portion 17, as should be apparent. Therefore, the appliance 12 of FIG. 3 tends to rotate the bracket 15 in the counterclockwise direction and to rotate the bracket 16 in the clockwise direction.

Other engaging means may be provided on the orthodontic loops of the present invention so as to provide substantially non-rotational engagement with a bracket and/or a tooth. FIG. 4 illustrates a loop-type member 18 with an interconnecting strand 19 integrally extending therefrom. Strand 19 is preferably connected to another loop-type member, either of the same type as loop 18 or of any other type. For example, the additional loop member may be of the type shown in the other Figures of the drawing. Only one loop is shown in FIG. 4 for ease of illustration. The loop 18 has a central portion 20 which is of substantially thinner material than the portion designated by 18. See FIG. 5. The relatively thin central material 20 has slits 21 formed therein. The number of slits 21 may vary, depending upon application. When the loop 18 is stretched to fit around a bracket, such as bracket 8 of FIG. 1, the slits 21 cause the central material 20 to function substantially equivalently to the nodules 13 and 14 of FIG. 3 or the nodules 4, 5, 6 of FIG. 1 so as to non-rotationally engage the loop 18 with a bracket.

FIG. 6 shows a loop 22 with nodules 23 formed on the inner surface thereof. In many applications, forming the nodules on the inner surface of the loop is preferable since better engagement with the engaging surfaces 10, 11 of the bracket is possible. With inner nodules or protuberances, such as shown in FIGS. 4 and 6, improved engagement is achieved over the type shown in FIG. 1. The connecting strand 24, which is integral with loop 22 is preferably connected with additional loop members which are not shown for ease of illustration.

FIG. 7 illustrates a further modification of the invention wherein a loop 25 has a serrated inner surface 26 which serves as the engagement means for engaging the engaging and retaining surfaces 10, 11 of a bracket when the loop member 25 is stretched around the bracket to engage the opening 7 of the bracket. In addition to the inner surface 26, the side and possibly the outer surfaces may also be made serrated or undulated so as to serve as engagement means.

FIG. 8 illustrates a further modification of the invention wherein a loop member 27 has nodules 28, 29 on the side surfaces thereof. The nodules or protuberances 28, 29 engage the surfaces 10, 11 to non-rotationally secure the loop 27 to the bracket 8. As shown in FIG. 9, the loop 27 may have nodules or protuberances 28 on one side thereof, or as shown in FIG. 10, nodules or protuberances 29 may be provided on opposite sides of the loop 27. If desired, nodules may also be provided on the inner surface of loop 27 in combination with either the nodule arrangement 28 or the nodule arrangement 29.

FIG. 11 illustrates a further modification according to the present invention wherein a loop type member 30 has a plurality of slits 31 extending outwardly from the inner surface thereof. When the loop 30 is stretched over the bracket to engage same, the material around the slits 31 is deformed and performs a similar function as the nodules 23 (FIG. 6) to engage at least one of the surfaces 10, 11 of a bracket 8 as shown in FIG. 2.

FIG. 12a illustrates a still further embodiment of the present invention wherein the cross-sectional dimension of a loop 32 is substantially larger than the opening 7 defined by the bracket. In accordance with the concept of FIG. 12, the loop 32 is substantially stretched in order to fit same over the bracket and into the bracket opening 7. The stretching of the loop is to such a degree that when in the extremely stretched condition, a portion of the loop 32 will fit within the opening 7. When the loop is released, it will contract. The portion of the loop 32 already within the opening 7 is restrained, so the portions of the loop 32 outside of the opening 7 will effectively be substantially bulged outwardly so as to provide a similar non-rotational engagement with the bracket as the devices heretofore described. FIG. 12b shows the loop 32 mounted on a bracket 8, clearly illustrating the bulging portions which prevent rotation of the loop 32 relative to the bracket 8. The loop 32 may have a substantially oval cross-sectional shape as shown in FIG. 13a, may have a generally circular cross-sectional shape, or may have a non-uniform cross-sectional shape as shown in FIG. 13b. In FIG. 13b, the outward portion of the loop 32 is of substantially larger cross-sectional dimension than the inner portion 32a thereof.

As shown in FIG. 14, a loop 33 may be provided with substantially annular protuberance means 34 so as to provide engagement with surfaces of the bracket, such as surfaces 10, 11 as shown in FIG. 1.

In all of the embodiments above-described, it should be clear that the loops may be provided singly with a strand member extending therefrom, may be provided doubly with an interconnecting strand therebetween, or may be provided in a continuous chain which may be completely utilized or cut in sections as desired. Such a continuous chain of loop members is shown, for example in FIG. 1. The loops in FIG. 1 may be interchanged with any of the other above-described loop members.

FIG. 15 illustrates the embodiment of FIG. 6 when attached to a pair of brackets in a preferred manner. First, one of the loops 22 is tightly engaged on a bracket 8, protuberance means 23 engaging surfaces such as surfaces 10, 11 of the bracket 8. The connecting strand 24 is wrapped around the outer portion thereof and is simultaneously stretched. With the connecting strand 24 in its stretched out condition, the other loop 22 is engaged with a second bracket, the protuberances 23 thereof non-rotationally engaging the loop with the bracket. As a result, in the construction shown in FIG. 15, the bracket 8a is rotated in the counterclockwise direction, and the bracket 8b is caused to rotate in the clockwise direction. The appliance of FIG. 15 is shown with spaces between adjacent surfaces and between surfaces of the brackets for ease of understanding of the inventive concept. In practice, however, the appliance is extremely tightly engaged or wrapped around the respective brackets.

FIG. 16 illustrates the use of an appliance, such as the appliance of FIG. 6, directly on two teeth 35, 36, which may be adjacent each other or spaced apart. One of the loop-type members 22 is stretched so as to tightly engage the tooth 35, the nodules 23 being very tightly pressed against the outer surfaces of the tooth to effectively non-rotationally engage the loop 22 with the tooth. The connecting strand 24 is preferably wrapped around a portion of the tooth in its stretched condition and the other loop 22 is engaged with the other tooth 36, again with the strand preferably wrapped around an outer surface of the tooth so as to provide very high restoring forces in the interconnecting strand 24 to tend to rotate the teeth about their longitudinal axes. The tooth 35 will tend to rotate in the clockwise direction and the tooth 36 will tend to rotate in the counterclockwise direction when the appliance is used as shown in FIG. 16.

It should be clear that the examples shown in FIGS. 15 and 16 are given merely by way of illustration and that the other loop-type members illustrated in the drawings may be used in place of the loops 22 of FIG. 6.

FIG. 17 illustrates an embodiment of the invention utilizing a single elastic loop 37 having protuberances 38 thereon. The protuberances may be any of the other types shown in the drawing or may be replaced by any of the other types of engaging means shown in the drawings. The elastic loop 37 has an elastic strand 39 preferably intergrally formed therewith. The elastic strand 39 has protuberance means 40 thereon which, in FIG. 17, are generally triangular in shape. The protuberances may be as shown in FIG. 17 and are of the general type described and illustrated in my copending application Ser. No. 566,752 or in U.S. Pat. No. 3,879,850. The protuberances 40 may be dimensioned such that they are larger or smaller than a channel opening into which the strand portion is to be received. The strand portion 39 may be any length, as indicated by broken lines in FIG. 17, and may be cut to size by the operator as desired.

FIG. 18 illustrates a modification of the arrangement of FIG. 17 wherein the loop 30 having slits 31 therein is integrally formed with a strand 41 having protuberances 42 thereon. Again, the protuberances 42 are preferably designed to meet the constraints set forth in my copending application Ser. No. 566,752 or in U.S. Pat. No. 3,879,850. It should be clear that any other type of strand, meeting the constraints of said prior application and patent can be used.

In use, the arrangement of FIG. 17 is used similarly as the heretofore described embodiments. For example, using the embodiment of FIG. 17 in the example of FIG. 15, the loop 37 would be engaged with a bracket in a similar manner as the loop 22. The strand 39 would then be stretched and arranged in a similar manner as the interconnecting strand 24 of FIG. 15. The end of the strand, or any intermediate portion thereof, can then be engaged with a bracket or other engaging member in order to retain tension on the strand 39. The engagement of the strand 39 with a bracket or other retaining member is in a similar manner as shown in my copending application Ser. No. 566,752 or in my U.S. Pat. No. 3,879,850. Similarly, the embodiments of FIGS. 17 and 18 may be used to rotate a tooth, such as tooth 35 of FIG. 16. In this application, the elastic loop is engaged with a tooth in the same manner as loop 22 is engaged with tooth 35 in FIG. 16, and the elastic strand 39 is stretched and anchored at an appropriate point to provide the appropriate rotational forces to the tooth on which the elastic loop 37 is engaged.

It should be clear that the embodiments of FIGS. 17 and 18 are exemplary and they may be varied within the scope of the invention as defined in the appended claims. Any of the specific elastic loops shown in the drawings may be used in the embodiments of FIGS. 17 and 18, as well as other variations which would be apparent to those skilled in the art, and any of the elastic strands shown and described in my copending application Ser. No. 566,752 or my U.S. Pat. No. 3,879,850 may be used, as well as apparent modifications thereof.

The engaging means on the elastic loops and strands, such as the nodules, serrated surfaces, or other protuberance means, may be made in other forms than shown in the drawings. Moreover, any number of nodules or protuberance means may be provided on the loops, as desired and the cross-sectional shapes of the loops and/or the engaging means may take any convenient form other than the circular, oval or other forms illustrated in the drawings. For example, the devices may be punched from substantially flat materials or may be molded in any desired shape. The substantially serrated inner surface 26 of FIG. 7 may take any other irregular, roughened or undulated shape. Symmetrical as well as non-symmetrical arrangements may be provided. Arrangements may be provided with any number of loops, which may be separated by smooth elastic strands, or which may be separated by strands such as strands 39 or 41 of FIGS. 17 and 18, respectively, or which may be connected together by smooth strands and have an additional strand such as strand 39 or 41 connected thereto.

FIG. 19 illustrates still another embodiment of the elastic appliance according to the present invention which comprises a loop of elastic material which may be similar to the loops previously discussed, with protuberances 44 and 45 extending from a surface thereof. FIG. 19 illustrates the elastic loop 43 mounted on a bracket 46 which in turn is mounted to a band 47 which is mounted on a tooth (not shown) in a conventional manner. An arch wire 48 extends through the central opening 49 of the bracket and passes under the elastic loop 43. Nodule 44 is arranged such that it bears against the arch wire 48 and nodule 45 is arranged such that it bears against an opening portion of the channel defined by the bracket 46 in which the elastic loop 43 is mounted. The bracket 46 of FIG. 19 is of the conventional type generally shown in side view in FIG. 2. The elastic loop 43 of FIG. 19 is mounted on the bracket such that it is stretched to impart clockwise rotation to the bracket 46 relative to the arch wire. This rotation is obtained by virtue of the resiliency of the elastic loop 43 and the location of the protuberances 44, 45 relative to the bracket and arch wire. The elastic loop 46 is shown in an exaggerated form in FIG. 19. In reality, it will be tightly stretched over the bracket 46.

FIGS. 20-22 show modified embodiments of elastic loops according to the present invention. In FIG. 20, elastic loop 50 has externally directed protuberances 51 and an internally directed protuberance 52. This arrangement is merely shown by way of example as being exemplary of numerous alternative constructions which could be provided to provide similar results within the inventive concept. In FIG. 21, four protuberances 53 are provided on an elastic loop 54. Again, this illustration is merely by way of example and is only exemplary of many possible variations.

FIG. 22 illustrates an elastic loop 55 having an external protuberance 56 thereon which is particularly adapted for abutting against a bracket, or the like, such as protuberance 45 in FIG. 19. The elastic loop 55 has a cut-out portion or depression 57 therein which is particularly adapted to engage an arch wire, such as arch wire 48. FIG. 23 shows in enlarged from the cross-section of the portion of the elastic loop 55 having the depression 57 therein. The depression 57 in FIGS. 22 and 23 serves the function of the protuberance 44 in FIG. 19 since it cooperates with the arch wire to provide a relative rotation to the bracket about the arch wire.

It should be clear that various modifications and alterations could be made to the embodiments shown in FIGS. 19-23. For example, the protuberances may be replaced by any of the other bracket engaging means illustrated in the prior figures, or may be replaced by any other of the tooth engaging means illustrated in the prior figures so that the elastic loop could be usable as non-rotatably mounted about a tooth, for example as shown in FIG. 16, with another protuberance means, or the like, being wedged against a fixed object in the mouth, such as an arch wire, bracket or other tooth, so as to impart a relative rotation to a tooth about the longitudinal axis thereof. In FIG. 19, for example, the protuberance 44 may be formed with a notch or other surface configuration to engage arch wire 48 or another appliance in the mouth. Still further, the protuberance 44 may have pin, tie wire or other engaging means to positively secure the wire 48, or the like, thereto. The protuberance 44 may be shaped like a bracket, for example. The loop 43 is also useful when engaged with a tooth such as shown in FIG. 6.

The embodiments of FIGS. 19-23, while being shown for single elastic loops which are functional by themselves, may be used in connection with elastic strands, such as strand 39 or 41 of FIGS. 17 or 18, or may be used in chains, such as shown in FIG. 1. Numerous combinations are obtainable by combining various of the embodiment in any desired form to provide a desired result in a given situation, within the spirit and scope of the present invention. Various other modifications and alterations to the illustrated embodiments should be apparent to those ordinarily skilled in the art.

FIG. 24 shows still another modified embodiment of the present invention wherein the means for applying a force to the loop relative to the bracket on which the loop is mounted comprises a large protuberance or wedge 58 which is integral with a loop 59 of elastic material. Loop 59 has protuberances 60, 61 extending therefrom so as to non-rotatably retain the loop 59 relative to a bracket or tooth on which it is mounted. Alternatively, the protuberances 60, 61 could be eliminated and the wedge or large protuberance 58 may be dimensioned such that it will serve not only to apply force to the loop, but will also engage a portion of a bracket opening so as to non-rotatably retain the loop in position relative to the bracket on which it is mounted.

FIG. 25 illustrates a further modification of the invention for use with two brackets which may or may not be adjacent each other. The loop 62 is mounted to a bracket 63 and the wedge member 64 is engaged between the arch wire 65 and a surface of a tooth, either directly or through the intermediary of a band which is mounted on the tooth. Due to the slippery conditions within the mouth, and the high forces involved, the pressure on the wedge 64 between the tooth surface and the arch wire 65 could possibly tend to cause the wedge to come out of engagement. The nodules 66 on the loop 62 non-rotatably retain the loop in position relative to the bracket 63 to prevent such disengagement of the wedge 64. As mentioned above with respect to FIG. 24, the nodules 66 could be eliminated and the wedge 64 could be made larger so that the upper and lower extremities thereof would also bear against a portion of the bracket 63 to prevent the loop 62 from rotating relative to the bracket. A further loop 67 is coupled to loop 62, for example by means of an elastic connecting strand 68. Loop 67 may be used, for example, as shown in FIG. 25, to impart rotational forces to a tooth on which the bracket 69 is mounted. It should be clear that brackets 63 and 69 could be mounted on the same or different teeth.

FIG. 6 shows a still further modification of the invention comprising three loops 70, 71 and 72 integrally connected together in a chain. The arrangement of FIG. 26 is shown with two loops having protuberances thereon with a third loop having no protuberances or other engaging means. This modification is shown only by way of example and it should be clear that any combination of loops, with or without bracket or tooth engaging means, and provided in any form, could be used. The arrangement of FIG. 26 is merely exemplary to illustrate another utilitarian embodiment of the invention.

In FIGS. 24-26, specific protuberances and wedge means are illustrated. However, it should be clear that any of the engaging means of the present invention, to prevent relative movement between an elastic loop and either a bracket or a tooth could be used with any of the embodiments of FIGS. 24-26, as should be apparent to those skilled in the art. For example, the embodiments of FIGS. 24-26 may be used directly on a tooth similar to the manner shown in FIG. 16. In this instance, the wedge 58, 64 could be used either between the tooth and another appliance in the mouth, or between two adjacent teeth, as desired. The wedge 58, 64 is shown only by way of example, and may take any desired shape to perform the result described above.

The above embodiments are given merely by way of example and are not to be deemed as limiting of the inventive concept as defined in the appended claims.

I claim:

1. An orthodontic elastic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:

a plurality of closed loops of elastic material;

at least one of the said elastic closed loops being adapted to at least partially pass through at least a portion of an opening of a bracket means and be mounted on the bracket means;

elastic connecting means coupled between adjacent closed loops for applying a force to said at least one elastic closed loop relative to a bracket means on which said at least one elastic loop is mounted, said force having a rotational component at least in the plane of said at least one elastic closed loop; and at least one protuberance extending from a surface of at least one of said elastic loops, said at least one protuberance and said at least one elastic loop being dimensioned and shaped such that when said at least one elastic loop is stretched and is at least partially engaged in an opening defined by one of said bracket means, said at least one protuberance of said at least one elastic loop abuttingly engages at least a portion of said at least one engaging and retaining surface of said bracket means to substantially prevent said engaged elastic loop from shifting its position relative to the bracket means on which it is mounted under the influence of said rotational component of said applied force.

2. An orthodontic elastic appliance according to claim 1 wherein said at least one protuberance has a maximum cross-sectional dimension, when mounted to a bracket, not larger than the predetermined cross-sectional dimension of said opening defined by said bracket means.

3. An orthodontic elastic appliance according to claim 1 comprising a plurality of said protuberances distributed about a peripheral surface of said at least one elastic loop.

4. An orthodontic elastic appliance according to claim 3 wherein said protuberances are distributed about the inner peripheral surface of said at least one elastic loop.

5. An orthodontic elastic appliance according to claim 1, wherein said at least one protuberance comprises at least one generally annular ring-shaped elastic member extending from said at least one elastic loop and passing therearound.

6. An orthodontic elastic appliance according to claim 1, wherein said at least one protuberance comprises resilient surface means of said at least one elastic loop which is adapted to abuttingly engage at least a portion of said at least one engaging and retaining surface of said bracket means when said at least one elastic loop os stretchedly mounted to said bracket means.

7. An orthodontic elastic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:

a plurality of closed loops of elastic material;

at least one of the said elastic closed loops being adapted to at least partially pass through at least a portion of an opening of a bracket means and be mounted on the bracket means;

elastic connecting means coupled between adjacent closed loops for applying a force to said at least one elastic closed loop relative to a bracket means on which said at least one elastic loop is mounted, said force having a rotational component at least in the plane of said at least one elastic closed loop; and undulated surface means on at least one of said elastic loops defining a plurality of first and second surface portions which are high and low relative to each other, said undulated surface means and said at least one elastic loop being dimensioned and shaped such that when said at least one elastic loop is stretched and is at least partially engaged in an opening defined by one of said bracket means, a high portion of the undulations of said at least one elastic loop abuttingly engages at least a portion of said at least one engaging and retaining surface of said bracket means to substantially prevent said engaged elastic loop from shifting its position relative to the bracket means on which it is mounted under the influence of said rotational component of said applied force.

8. An orthodontic elastic appliance according to claim 7 wherein said undulated surface means is on at least the inner peripheral surface of said at least one elastic loop.

9. An orthodontic elastic appliance according to claim 7 wherein said undulated surface means is only on the inner peripheral surface of said at least one elastic loop.

10. An orthodontic elastic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:
a plurality of closed loops of elastic material;
at least one of the said elastic closed loops being adapted to at least partially pass through at least a portion of an opening of a bracket means and be mounted on the bracket means;
elastic connecting means coupled between adjacent closed loops for applying a force to said at least one elastic closed loop relative to a bracket means on which said at least one elastic loop is mounted, said force having a rotational component at least in the plane of said at least one elastic closed loop; and
abutment engaging means on a surface of at least one of said elastic loops, said abutment engaging means comprising an elastic central member extending from said at least one elastic loop and substantially filling the inner space defined by said at least one elastic loop, said central elastic member having at least one slit therein so as to define segments thereof, said segments and said at least one elastic loop being dimensioned and shaped such that when said at least one elastic loop is stretched and is at least partially engaged in an opening defined by one of said bracket means, at least one of said segments abuttingly engages at least a portion of said at least one engaging and retaining surface of said bracket means to substantially prevent said engaged elastic loop from shifting its position relative to the bracket means on which it is mounted under the influence of said rotational component of said applied force.

11. An orthodontic elastic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:
a plurality of closed loops of elastic material;
at least one of the said elastic closed loops being adapted to at least partially pass through at least a portion of an opening of a bracket means and be mounted on the bracket means;
elastic connecting means coupled between adjacent closed loops for applying a force to said at least one elastic closed loop relative to a bracket means on which said at least one elastic loop is mounted, said force having a rotational component at least in the plane of said at least one elastic closed loop; and
abutment engaging means on a surface of at least one of said elastic loops, said abutment engaging means comprising a plurality of slits in said at least one elastic loop, said slits extending from a peripheral surface thereof and partially through the cross-section of said at least one elastic loop, said at least one elastic loop and said slits therein being dimensioned and shaped such that when said at least one elastic loop is stretched and is at least partially engaged in an opening defined by one of said bracket means, the portion of said at least one elastic loop adjacent one of said slits abuttingly engages at least a portion of said at least one engaging and retaining surface of said bracket means to substantially prevent said engaged elastic loop from shifting its position relative to the bracket means which it is mounted under the influence of said rotational component of said applied force.

12. An orthodontic elastic appliance according to claim 11 wherein said slits extend from at least the inner peripheral surface of said at least one elastic loop.

13. An orthodontic elastic appliance mountable on teeth, comprising:
a plurality of closed loops of elastic material, at least one of said elastic closed loops having an inner periphery substantially smaller than the outer periphery of a tooth on which it is to be mounted;
elastic connecting means coupled between adjacent elastic closed loops for applying a force to said at least one elastic closed loop relative to the tooth on which said at least one elastic loop is mounted, said force having a rotational component at least in the plane of said at least one elastic closed loop; and
at least one protuberance extending from at least an inner surface of said at least one elastic loop, said at least one protuberance and said at least one elastic loop being dimensioned and shaped such that when said at least one elastic loop is stretched and is engaged around the outer periphery of a tooth said at least one protuberance of said at least one elastic loop abuttingly and non-slidingly engages at least a portion of the outer periphery of said tooth to substantially prevent said stretched and engaged elastic loop from shifting its position relative to a tooth around which it is mounted under the influence of said rotational component of said applied force.

14. An orthodontic elastic appliance according to claim 13 comprising at least two protuberances extending from opposing surfaces of said at least one elastic loop for non-slidingly engaging respective surfaces of a tooth.

15. An orthodontic elastic appliance according to claim 13 comprising a plurality of said protuberances distributed about the periphery of said at least one elastic loop.

16. An orthodontic elastic appliance according to claim 15 wherein said protuberances are distributed about the inner peripheral surface of said at least one elastic loop.

17. An orthodontic elastic appliance according to claim 13, wherein said at least one protuberance comprises at least one generally annular ring-shaped elastic member extending from said at least one elastic loop and passing therearound.

18. An orthodontic elastic appliance mountable on teeth, comprising:

a plurality of closed loops of elastic material, at least one of said elastic closed loops having an inner periphery substantially smaller than the outer periphery of a tooth on which it is to be mounted;

elastic connecting means coupled between adjacent elastic closed loops for applying a force to said at least one elastic closed loop relative to the tooth on which said at least one elastic loop is mounted, said force having a rotational component at least in the plane of said at least one elastic closed loop; and undulated surface means on at least an inner surface of said at least one elastic loop defining a plurality of first and second surface portions which are high and low relative to each other, said undulated surface means and said at least one elastic loop being dimensioned and shaped such that when said at least one elastic loop is stretched and is engaged around the outer periphery of a tooth, a high portion of the undulations of said at least one elastic loop abuttingly and non-slidingly engages at least a portion of the outer periphery of said tooth to substantially prevent said stretched and engaged elastic loop from shifting its position relative to a tooth around which it is mounted under the influence of said rotational component of said applied force.

19. An orthodontic elastic appliance mountable on teeth, comprising:

a plurality of closed loops of elastic material at least one of said elastic closed loops having an inner periphery substantially smaller than the outer periphery of a tooth on which it is to be mounted;

elastic connecting means coupled between adjacent elastic closed loops for applying a force to said at least one elastic closed loop relative to the tooth on which said at least one elastic loop is mounted, said force having a rotational component at least in the plane of said at least one elastic closed loop; and abutment engaging means on at least an inner surface of said at least one elastic loop, said abutment engaging means comprising an elastic central member extending from said at least one elastic loop and filling at least a substantial portion of the inner space defined by said at least one elastic loop, said central elastic member having at least one slit therein so as to define segments thereof, said segments and said at least one elastic loop being dimensioned and shaped such that when said at least one elastic loop is stretched and is engaged around the outer periphery of a tooth, at least one of said segments abuttingly and non-slidingly engages at least a portion of the outer periphery of said tooth to substantially prevent said stretched and engaged elastic loop from shifting its position relative to a tooth around which it is mounted under the influence of said rotational component of said applied force.

20. An orthodontic elastic appliance mountable on teeth, comprising:

a plurality of closed loops of elastic material, at least one of said elastic closed loops having an inner periphery substantially smaller than the outer periphery of a tooth on which it is to be mounted;

elastic connecting means coupled between adjacent elastic closed loops for applying a force to said at least one elastic closed loop relative to the tooth on which said at least one elastic loop is mounted, said force having a rotational component at least in the plane of said at least one elastic closed loop; and abutment engaging means on at least an inner surface of said at least one elastic loop, said abutment engaging means comprising a plurality of slits in said at least one elastic loop, said slits extending from the inner peripheral surface thereof and partially through the cross-section of said at least one elastic loop, said at least one elastic loop and slits therein being dimensioned and shaped such that when said at least one elastic loop is stretched and is engaged around the outer periphery of a tooth, the portion of said at least one elastic loop adjacent one of said slits abuttingly and non-slidingly engages at least a portion of the outer periphery of said tooth to substantially prevent said stretched and engaged elastic loop from shifting its position relative to a tooth around which it is mounted under the influence of said rotational component of said applied force.

21. An orthodontic elastic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:

a plurality of closed loops of elastic material;

at least one of the said elastic closed loops being adapted to at least partially pass through at least a portion of an opening of a bracket means and be mounted on the bracket means;

elastic connecting means coupled between adjacent closed loops for applying a force to said at least one elastic closed loop relative to a bracket means on which said at least one elastic loop is mounted, said force having a rotational component at least in the plane of said at least one elastic closed loop; and at least one of said loops, in the relaxed state, having a cross-section over substantially the complete extent of the loop which is substantially larger than the cross-section of said opening defined by said bracket means, and being stretchable to reduce the cross-section of said at least one closed loop to fit at least partially within said opening defined by said bracket means, and the inner opening of said at least one closed loop, when in its relaxed state, being substantially smaller than the opening required to engage and be mounted on said bracket means;

said at least one elastic loop when relaxed after being stretched and mounted on said bracket means, having a portion thereof which bulges outwardly relative to said bracket means to abuttingly engage said at least one engaging and retaining surface of said at least one bracket means to substantially prevent said engaged elastic loop from shifting its position relative to the bracket means on which it is mounted under the influence of said rotational component of said applied force.

22. An orthodontic elastic appliance according to claim 21 wherein said at least one elastic loop has a substantially oval cross-section over substantially the complete extent of said loop.

23. An orthodontic elastic appliance according to claim 21 wherein said at least one elastic loop, over substantially the complete extent of said loop, has an innermost cross-section which is substantially reduced relative to the outermost cross-sectional portion thereof.

24. An orthodontic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:
at least one closed loop of elastic material;
said at least one closed loop being adapted to at least partially pass through at least a portion of an opening of a bracket means and be mounted on the bracket means;
means coupled to said at least one elastic closed loop for applying a force to said at least one elastic loop relative to the bracket means on which said loop is mounted, said force having a rotational component at least in the plane of said at least one elastic closed loop; and
at least one protuberance extending from a surface of said at least one elastic loop, said at least one protuberance and said at least one elastic loop being dimensioned and shaped such that when said at least one elastic loop is stretched and is at least partially engaged in an opening defined by one of said bracket means, said at least one protuberance of said at least one elastic loop abuttingly engages at least a portion of said at least one engaging and retaining surface of said bracket means to substantially prevent said engaged elastic loop from shifting its position relative to the bracket means on which it is mounted under the influence of said rotational component of said applied force.

25. An orthodontic elastic appliance according to claim 24 wherein said means for applying a force to said elastic loop includes an elastic strand means coupled to said at least one closed loop, said elastic strand means comprising an elongated elastic member having alternately arranged portions of larger and smaller dimensions relative to a substantially straight and substantially central axial line passing through the elongated elastic member which it is in a straight condition, said dimensions being taken in the same direction in a common plane containing said substantially straight axial line.

26. An orthodontic elastic appliance according to claim 25 wherein said larger dimension portions are dimensioned such that when said elongated elastic member is stretched along its length and is at least partially engaged in an opening defined by at least one orthodontic bracket means, said larger dimension portion abuttingly engages at least a portion of at least one engaging and retaining surface of the bracket means to substantially prevent the stretched elongated elastic member from relaxing.

27. An orthodontic elastic appliance according to claim 25 wherein said larger dimension portions of said elastic strand means comprise protuberance means thereon.

28. An orthodontic elastic appliance according to claim 24 wherein said at least one protuberance extending from said at least one elastic loop has a maximum cross-sectional dimension, when mounted to a bracket, not larger than the predetermined cross-sectional dimension of said opening defined by said bracket means.

29. An orthodontic elastic appliance according to claim 24 wherein said means for applying a force to said elastic loop includes at least one further protuberance extending from said at least one elastic loop.

30. An orthodontic elastic appliance according to claim 29 wherein said at least one further protuberance is adapted to bear against a fixed object in the mouth.

31. An orthodontic elastic appliance according to claim 30 wherein said at least one further protuberance is adapted to bear against an arch wire, or the like.

32. An orthodontic elastic appliance according to claim 31 wherein said at least one further protuberance includes means for engaging an arch wire, or the like.

33. An orthodontic elastic appliance according to claim 29 wherein said at least one further protuberance is of elastic material and is integrally formed with said at least one closed loop.

34. An orthodontic elastic appliance according to claim 29 wherein said at least one further protuberance is adapted to bear against a tooth.

35. An orthodontic elastic appliance according to claim 24 wherein said at least one protuberance serves as both said abutment engaging means and said means for applying said force to said at least one elastic loop.

36. An orthodontic elastic appliance according to claim 24 wherein said means for applying a force to said elastic loop comprises means for engaging an arch wire, or the like.

37. An orthodontic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:
at least one closed loop of elastic material;
said at least one closed loop being adapted to at least partially pass through at least a portion of an opening of a bracket means and be mounted on the bracket means;
means coupled to said at least one elastic closed loop for applying a force to said at least one elastic loop relative to the bracket means on which said loop is mounted, said force having a rotational component at least in the plane of said at least one elastic closed loop; and
undulated surface means on at least a surface of said at least one elastic loop defining a plurality of first and second surface portions which are high and low relative to each other, said undulated surface means and said at least one elastic loop being dimensioned and shaped such that when said at least one elastic loop is stretched and is at least partially engaged in an opening defined by one of said bracket means, a high portion of the undulations of said at least one elastic loop abuttingly and non-slidingly engages at least a portion of said at least one engaging and retaining surface of said bracket means to substantially prevent said engaged elastic loop from shifting its position relative to the bracket means on which it is mounted under the influence of said rotational component of said applied force.

38. An orthodontic elastic appliance according to claim 37 wherein said undulated surface means is on at least the inner peripheral surface of said at least one elastic loop.

39. An orthodontic elastic appliance according to claim 37 wherein said means for applying a force to said elastic loop includes at least one protuberance extending from said at least one elastic loop.

40. An orthodontic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:
at least one closed loop of elastic material;
said at least one closed loop being adapted to at least partially pass through at least a portion of an opening of a bracket means and be mounted on the bracket means;
means coupled to said at least one elastic closed loop for applying a force to said at least one elastic loop relative to the bracket means on which said loop is mounted, said force having a rotational component at least in the plane of said at least one elastic closed loop; and
abutment engaging means on at least a surface of said at least one elastic loop, said abutment engaging means comprising a plurality of slits in said at least one elastic loop, said slits extending from a peripheral surface thereof and partially through the cross-section of said at least one elastic loop, said at least one elastic loop and said slits therein being dimensioned and shaped such that when said at least one elastic loop is stretched and is at least partially engaged in an opening defined by one of said bracket means, the portion of said at least one elastic loop adjacent one of said slits abuttingly and non-slidingly engages at least a portion of said at least one engaging and retaining surface of said bracket means to substantially prevent said engaged elastic loop from shifting its position relative to the bracket means on which it is mounted under the influence of said rotational component of said applied force.

41. An orthodontic elastic appliance according to claim 4 wherein said slits extend from at least the inner peripheral surface of said at least one elastic loop.

42. An orthodontic elastic appliance according to claim 40 wherein said means for applying a force to said elastic loop includes at least one protuberance extending from said at least one elastic loop.

43. An orthodontic elastic appliance mountable on a tooth, comprising:
at least one closed loop of elastic material having an inner periphery substantially smaller than the outer periphery of a tooth on which it is to be mounted;
means coupled to said at least one elastic loop for applying a force to said at least one elastic loop relative to a tooth on which said loop is mounted said force having a rotational component at least in the plane of said at least one elastic closed loop; and
at least one protuberance extending from an inner surface of said at least one elastic loop, said at least one protuberance and said at least one elastic loop being dimensioned and shaped such that when said at least one elastic loop is stretched and is engaged around the outer periphery of a tooth said at least one protuberance of said at least one elastic loop abuttingly and non-slidingly engages at least a portion of the outer periphery of said tooth to substantially prevent said stretched and engaged elastic loop from shifting its position relative to a tooth around which it is mounted under the influence of said rotational component of said applied force.

44. An orthodontic elastic appliance according to claim 43 wherein said means for applying a force to said elastic loop includes an elastic strand means coupled to said at least one closed loop, said elastic strand means comprising an elongated elastic member having alternately arranged portions of larger and smaller dimensions relative to a substantially straight and substantially central axial line passing through the elongated member when it is in a straight condition, said dimensions being taken in the same direction in a common plane containing said substantially straight axial line.

45. An orthodontic elastic appliance according to claim 44 wherein said larger dimension portions are dimensioned such that when said elongated elastic member is stretched along its length and is at least partially engaged in an engaging opening in the mouth, said larger dimension portion abuttingly engages at least a portion of said engaging opening to substantially prevent the stretched elongated elastic member from relaxing.

46. An orthodontic elastic appliance according to claim 45 wherein said engaging opening is at least partially defined by a bracket means mounted to a tooth.

47. An orthodontic elastic appliance according to claim 44 wherein said larger dimension portions of said elastic strand means comprise protuberance means thereon.

48. An orthodontic elastic appliance according to claim 45 wherein said larger dimension portions of said elastic strand means comprise protuberance means thereon.

49. An orthodontic elastic appliance according to claim 43 wherein said means for applying a force to said elastic loop includes at least one further protuberance extending from said at least one elastic loop.

50. An orthodontic elastic appliance according to claim 49 wherein said at least one further protuberance is adapted to bear against a fixed object in the mouth.

51. An orthodontic elastic appliance according to claim 50 wherein said at least one further protuberance is adapted to bear against an arch wire, or the like.

52. An orthodontic elastic appliance according to claim 51 wherein said at least one further protuberance includes means for engaging an arch wire, or the like.

53. An orthodontic elastic appliance according to claim 49 wherein said at least one further protuberance is of elastic material and is integrally formed with said at least one closed loop.

54. An orthodontic elastic appliance according to claim 49 wherein said at least one further protuberance is adapted to bear against a tooth.

55. An orthodontic elastic appliance according to claim 43 wherein said at least one protuberance serves as both said abutment engaging means and said means for applying said force to said at least one elastic loop.

56. An orthodontic elastic appliance according to claim 43 wherein said means for applying a force to said at least one elastic loop comprises means for engaging an arch wire, or the like.

57. An orthodontic elastic appliance mountable on a tooth, comprising:
at least one closed loop of elastic material having an inner periphery substantially smaller than the outer periphery of a tooth on which it is to be mounted;
means coupled to said at least one elastic loop for applying a force to said at least one elastic loop relative to a tooth on which said loop is mounted said force having a rotational component at least in the plane of said at least one elastic closed loop; and undulated surface means on at least an inner surface of said at least one elastic loop defining a plurality of first and second surface portions which are high and low relative to each other, said undulated surface means and said at least one elastic loop being dimensioned and shaped such that when said at least one elastic loop is stretched and is engaged around the outer periphery of a tooth, a high portion of the undulations of said at least one elastic loop abuttingly and non-slidingly engages at least a portion of the outer periphery of said tooth to substantially prevent said stretched and engaged elastic loop from shifting its position relative to a tooth around which it is mounted under the influence of said rotational component of said applied force.

58. An orthodontic elastic appliance according to claim 57 wherein said means for applying a force to said elastic loop includes at least one protuberance extending from said at least one elastic loop.

59. An orthodontic elastic appliance mountable on a tooth, comprising:

at least one closed loop of elastic material having an inner periphery substantially smaller than the outer periphery of a tooth on which it is to be mounted;

means coupled to said at least one elastic loop for applying a force to said at least one elastic loop relative to a tooth on which said loop is mounted said force having a rotational component at least in the plane of said at least one elastic closed loop; and abutment engaging means on at least an inner surface of said at least one elastic loop, said abutment engaging means comprising a plurality of slits in said at least one elastic loop, said slits extending from the inner peripheral surface thereof and partially through the cross-section of said at least one elastic loop, said at least one elastic loop and said slits therein being dimensioned and shaped such that when said at least one elastic loop is stretched and is engaged around the outer periphery of a tooth, the portion of said at least one elastic loop adjacent one of said slits abuttingly and non-slidingly engages at least a portion of the outer periphery of said tooth to substantially prevent said stretched and engaged elastic loop from shifting its position relative to a tooth around which it is mounted under the influence of said rotational component of said applied force.

60. An orthodontic elastic appliance according to claim 59 wherein said means for applying a force to said elastic loop includes at least one protuberance extending from said at least one elastic loop.

61. An orthodontic elastic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:

at least one closed loop of elastic material;

said at least one closed loop being adapted to at least partially pass through at least a portion of an opening of a bracket means and be mounted on the bracket means;

means coupled to said at least one elastic closed loop for applying a force to said at least one elastic loop relative to the bracket means on which said loop is mounted, said force having a rotational component at least in the plane of said at least one elastic closed loop; and said at least one closed loop, in the relazed state, having a cross-section over substantially the complete extent of the loop which is substantially larger than the cross-section of said opening defined by said bracket means, and being stretchable to reduce the cross-section of said at least one closed loop to fit at least partially within said opening defined by said bracket means, and the inner opening of said at least one closed loop, when in its relaxed state, being substantially smaller than the opening required to engage and be mounted on said bracket means;

said at least one elastic loop when relaxed after being stretched and mounted on said bracket means, having a portion thereof which bulges outwardly relative to said bracket means to abuttingly engage said at least one engaging and retaining surface of said at least one bracket means to substantially prevent said engaged elastic loop from shifting its position relative to the bracket means on which it is mounted under the influence of said rotational component of said applied force.

62. An orthodontic elastic appliance according to claim 61 wherein said means for applying a force to said at least one elastic loop includes an elastic strand means coupled to said elastic loop, said elastic strand means comprising an elongated elastic member having alternately arranged protions of larger and smaller dimensions relative to a substantially straight and substantially central axial line passing through the elongated elastic member when it is in a straight condition, said dimensions being taken in the same direction in a common plane containing said substantially straight axial line.

63. An orthodontic elastic appliance according to claim 62 wherein said larger dimension portions are dimensioned such that when said elongated elastic member is stretched along its length and is at least partially engaged in an opening defined by at least one orthodontic bracket means, said larger dimension portion abuttingly engages at least a portion of at least one engaging and retaining surface of the bracket means to substantially prevent the stretched elongated elastic member from relaxing.

64. An orthodontic elastic appliance according to claim 61 wherein said at least one elastic loop has a substantially oval cross-section over substantially the complete extent of said loop.

65. An orthodontic elastic appliance according to claim 61 wherein said at least one elastic loop, over substantially the complete extent of said loop, has an innermost cross-section which is substantially reduced relative to the outermost cross-sectional portion thereof.

66. An orthodontic elastic appliance according to claim 63 wherein said larger dimension portions of said elastic strand means comprise protuberance means thereon.

67. An orthodontic elastic appliance according to claim 61 wherein said means for applying a force to said at least one elastic loop includes at least one protuberance extending from said at least one elastic loop.

68. An orthodontic elastic appliance according to claim 67 wherein said at least one protuberance is adapted to bear against a fixed object in the mouth.

69. An orthodontic elastic appliance according to claim 68 wherein said at least one portuberance is adapted to bear against an arch wire, or the like.

70. An orthodontic elastic appliance according to claim 69 wherein said at least one protuberance includes means for engaging an arch wire, or the like.

71. An orthodontic elastic appliance according to claim 67 wherein said at least one protuberance is of elastic material and is integrally formed with said at least one closed loop.

72. An orthodontic elastic appliance according to claim 67 wherein said at least one protuberance is adapted to bear against a tooth.

73. An orthodontic elastic appliance according to claim 67 wherein said at least one protuberance serves as both an abutment engaging means for further preventing said engaged elastic loop from shifting in position and as said means for applying said force to said at least one elastic loop.

74. An orthodontic elastic appliance according to claim 61 wherein said means for applying a force to said at least one elastic loop comprises means for engaging an arch wire, or the like.

75. An orthodontic elastic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:

a plurality of closed loops of elastic material;

at least one of the said elastic closed loops being adapted to at least partially pass through at least a portion of an opening of a bracket means and be mounted on the bracket means;

elastic connecting means coupled between adjacent closed loops for applying a force to said at least one elastic closed loop relative to a bracket means on which said at least one elastic loop is mounted, said force having a rotational component at least in the plane of said at least one elastic closed loop; and serrated surface means on at least one of said elastic loops defining a plurality of first and second surface portions which are high and low relative to each other, said serrated surface means and said at least one elastic loop being dimensioned and shaped such that when said at least one elastic loop is stretched and is at least partially engaged in an opening defined by one of said bracket means, a high portion of the serrations of said at least one elastic loop abuttingly engages at least a portion of said at least one engaging and retaining surface of said bracket means to substantially prevent said engaged elastic loop from shifting its position relative to the bracket means on which it is mounted under the influence of said rotational component of said applied force.

76. An orthodontic elastic appliance according to claim 75 wherein said serrated means is on the inner surface of said at least one elastic loop.

77. An orthodontic elastic appliance mountable on teeth, comprising:

a plurality of closed loops of elastic material, at least one of said elastic closed loops having an inner periphery substantially smaller than the outer periphery of a tooth on which it is to be mounted;

elastic connecting means coupled between adjacent elastic closed loops for applying a force to said at least one elastic closed loop relative to the tooth on which said at least one elastic loop is mounted, said force having a rotational component at least in the plane of said at least one elastic closed loop; and serrated surface means on at least an inner surface of said at least one elastic loop defining a plurality of first and second surface portions which are high and low relative to each other, said serrated surface means and said at least one elastic loop being dimensioned and shaped such that when said at least one elastic loop is stretched and is engaged around the outer periphery of a tooth, a high portion of the serrations of said at least one elastic loop abuttingly and non-slidingly engages at least a portion of the outer periphery of said tooth to substantially prevent said stretched and engaged elastic loop from shifting its position relative to a tooth around which it is mounted under the influence of said rotational component of said applied force.

78. An orthodontic elastic appliance according to claim 77 wherein said serrated surface means is on the inner surface of said at least one elastic loop.

79. An orthodontic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:

at least one closed loop of elastic material;

said at least one closed loop being adapted to at least partially pass through at least a portion of an opening of a bracket means and be mounted on the bracket means;

means coupled to said at least one elastic closed loop for applying a force to said at least one elastic loop relative to the bracket means on which said loop is mounted, said force having a rotational component at least in the plane of said at least one elastic closed loop; and serrated surface means on at least a surface of said at least one elastic loop defining a plurality of first and second surface portions which are high and low relative to each other, said serrated surface means and said at least one elastic loop being dimensioned and shaped such that when said at least one elastic loop is stretched and is at least partially engaged in an opening defined by one of said bracket means, a high portion of the serratins of said at least one elastic loop abuttingly and non-slidingly engages at least a portion of said at least one engaging and retaining surface of said bracket means to substantially prevent said engaged elastic loop from shifting its position relative to the bracket means on which it is mounted under the influence of said rotational component of said applied force.

80. An orthodontic elastic appliance according to claim 79 wherein said serrated surface means is on the inner surface of said at least one elastic loop.

81. An orthodontic elastic appliance mountable on a tooth, comprising:

at least one closed loop of elastic material having an inner periphery substantially smaller than the outer periphery of a tooth on which it is to be mounted;

means coupled to said at least one elastic loop for applying a force to said at least one elastic loop relative to a tooth on which said loop is mounted said force having a rotational component at least in the plane of said at least one elastic closed loop; and serrated surface means on at least an inner surface of said at least one elastic loop defining a plurality of first and second surface portions which are high and low relative to each other, said serrated surface means and said at least one elastic loop being dimensioned and shaped such that when said at least one elastic loop is stretched and is engaged around the outer periphery of a tooth, a high portion of the serrations of said at least one elastic loop abuttingly and non-slidingly engages at least a portion of the outer periphery of said tooth to substantially prevent said stretched and engaged elastic loop from shifting its position relative to a tooth around which it is mounted under the influence of said rotational component of said applied force.

82. An orthodontic elastic appliance according to claim 81 wherein said serrated surface is on the inner surface of said at least one elastic loop.

83. An orthodontic elastic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:

a plurality of closed loops of elastic material;

at least one of the said elastic closed loops being adapted to at least partially pass through at least a portion of an opening of a bracket means and be mounted on the bracket means, elastic connecting means coupled between adjacent closed loops for applying a force to said at least one elastic closed loop relative to a bracket means on which said at least one elastic loop is mounted, said force having a rotational component at least in the plane of said at least one elastic closed loop; and irregular surface engaging means on a surface of at least one of said elastic loops defining first and second surface portions which are high and low relative to each other and defining at least one portion extending away from the remainder of the surface thereof, said irregular surface engaging means and said at least one elastic loop being dimensioned and shaped such that when said at least one elastic loop is stretched and is at least partially engaged in an opening defined by one of said bracket means, said irregular surface engaging means of said at least one elastic loop interferingly engages at least a portion of said at least one engaging and retaining surface of said bracket means to substantially prevent said engaged elastic loop from shifting its position relative to the bracket means on which it is mounted under the influence of said rotational component of said applied force.

84. An orthodontic elastic appliance mountable on teeth, comprising:

a plurality of closed loops of elastic material, at least one of said elastic closed loops having an inner periphery substantially smaller than the outer periphery of a tooth on which it is to be mounted;

elastic connecting means coupled between adjacent elastic closed loops for applying a force to said at least one elastic closed loop relative to the tooth on which said at least one elastic loop is mounted, said force having a rotational component at least in the plane of said at least one elastic closed loop; and irregular surface engaging means on an inner surface of said at least one elastic loop defining first and second surface portions which are high and low relative to each other and defining at least one portion extending away from the remainder of the surface thereof, said irregular surface engaging means and said at least one elastic loop being dimensioned and shaped such that when said at least one elastic loop is stretched and is engaged around the outer periphery of a tooth said engaging means of said at least one elastic loop non-slidingly engages at least a portion of the outer periphery of said tooth to substantially prevent said stretched and engaged elastic loop from shifting its position relative to a tooth around which it is mounted under the influence of said rotational component of said applied force.

85. An orthodontic appliance for use with orthodontic bracket means mountable on teeth, said bracket means defining an opening of predetermined cross-sectional dimension adapted to receive at least a portion of the orthodontic elastic appliance therein, the bracket opening defined by at least one of said bracket means having at least one engaging and retaining surface adjacent thereto, said elastic appliance comprising:

at least one closed loop of elastic material;

said at least one closed loop being adapted to at least partially pass through at least a portion of an opening of a bracket means and be mounted on the bracket means;

means coupled to said at least one elastic closed loop for applying a force to said at least one elastic loop relative to the bracket means on which said loop is mounted, said force having a rotational component at least in the plane of said at least one elastic closed loop; and irregular surface engaging means on a surface of said at least one elastic loop defining first and second surface portions which are high and low relative to each other and defining at least one portion extending away from the remainder of the surface thereof, said engaging means and said at least one elastic loop being dimensioned and shaped such that when said at least one elastic loop is stretched and is at least partially engaged in an opening defined by one of said bracket means, said engaging means of said at least one elastic loop engages at least a portion of said at least one engaging and retaining surface of said bracket means to substantially prevent said engaged elastic loop from shifting its position relative to the bracket means on which it is mounted under the influence of said rotational component of said applied force.

86. An orthodontic elastic appliance mountable on a tooth, comprising:

at least one closed loop of elastic material having an inner periphery substantially smaller than the outer periphery of a tooth on which it is to be mounted;

means coupled to said at least one elastic loop for applying a force to said at least one elastic loop relative to a tooth on which said loop is mounted, said force having a rotational component at least in the plane of said at least one elastic closed loop; and irregular surface engaging means on an inner surface of said at least one elastic loop defining first and second surface portions which are high and low relative to each other and defining at least one portion extending away from the remainder of the surface thereof, said irregular surface engaging means and said at least one elastic loop being dimensioned and shaped such that when said at least one elastic loop is stretched and is engaged around the outer periphery of a tooth said engaging means of said at least one elastic loop non-slidingly engages at least a portion of the outer periphery of said tooth to substantially prevent said stretched and engaged elastic loop from shifting its position relative to a tooth around which it is mounted under the influence of said rotational component of said applied force.

87. An orthodontic elastic appliance according to claim 57 wherein said means for applying a force to said elastic loop includes an elastic strand means coupled to said at least one closed loop, said elastic strand means comprising an elongated elastic member having alternately arranged portions of larger and smaller dimensions relative to a substantially straight and substantially central axial line passing through the elongated member when it is in a straight condition, said dimensions being taken in the same direction in a common plane containing said substantially straight axial line.

88. An orthodontic elastic appliance according to claim 59 wherein said means for applying a force to said elastic loop includes an elastic strand means coupled to said at least one closed loop, said elastic strand means comprising an elongated elastic member having alternately arranged portions of larger and smaller dimensions relative to a substantially straight and substantially central axial line passing through the elongated member when it is in a straight condition, said dimensions being taken in the same direction in a common plane containing said substantially straight axial line.

89. An orthodontic elastic appliance according to claim 79 wherein said means for applying a force to said elastic loop includes an elastic strand means coupled to said at least one closed loop, said elastic strand means comprising an elongated elastic member having alternately arranged portions of larger and smaller dimensions relative to a substantially straight and substantially central axial line passing through the elongated member when it is in a straight condition, said dimensions being taken in the same direction in a common plane containing said substantially straight axial line.

90. An orthodontic elastic appliance according to claim 81 wherein said means for applying a force to said elastic loop includes an elastic strand means coupled to said at least one closed loop, said elastic strand means comprising an elongated elastic member having alternately arranged portions of larger and smaller dimensions relative to a substantially straight and substantially central axial line passing through the elongated member when it is in a straight condition, said dimensions being taken in the same direction in a common plane containing said substantially straight axial line.

91. An orthodontic elastic appliance according to claim 85 wherein said means for applying a force to said elastic loop includes an elastic strand means coupled to said at least one closed loop, said elastic strand means comprising an elongated elastic member having alternately arranged portions of larger and smaller dimensions relative to a substantially straight and substantially central axial line passing through the elongated member when it is in a straight condition, said dimensions being taken in the same direction in a common plane containing said substantially straight axial line.

92. An orthodontic elastic appliance according to claim 86 wherein said means for applying a force to said elastic loop includes an elastic strand means coupled to said at least one closed loop, said elastic strand means comprising an elongated elastic member having alternately arranged portions of larger and smaller dimensions relative to a substantially straight and substantially central axial line passing through the elongated member when it is in a straight condition, said dimensions being taken in the same direction in a common plane containing said substantially straight axial line.

* * * * *

UNITED STATES PATENT AND TRADEMARK OFFICE
CERTIFICATE OF CORRECTION

PATENT NO. : 4,054,997
DATED : October 25, 1977
INVENTOR(S) : Melvin WALLSHEIN

It is certified that error appears in the above-identified patent and that said Letters Patent are hereby corrected as shown below:

Column 12, line 18, after "bracket means" insert --on--;

Column 17, line 42, change "claim 4" to --claim 40--;

Column 20, line 7, change "relazed" to --relaxed--.

Signed and Sealed this

Seventh Day of March 1978

[SEAL]

Attest:

RUTH C. MASON
Attesting Officer

LUTRELLE F. PARKER
Acting Commissioner of Patents and Trademarks